United States Patent [19]

Teuber et al.

[11] Patent Number: 5,554,632
[45] Date of Patent: Sep. 10, 1996

[54] BENZIMIDAZOLE COMPOUNDS

[75] Inventors: Lene Teuber, Varlose, Denmark; Oskar Axelsson, Malmo, Sweden; Frank Watjen, Herlev, Denmark

[73] Assignees: NeuroSearch A/S, Glostrup, Denmark; Meiji Seika Kaisha, Ltd., Tokyo, Japan

[21] Appl. No.: 352,585

[22] Filed: Dec. 9, 1994

Related U.S. Application Data

[62] Division of Ser. No. 207,774, Mar. 8, 1994, abandoned.

[30] Foreign Application Priority Data

Mar. 24, 1993 [DK] Denmark ................................ 0337/93
Sep. 21, 1993 [DK] Denmark ................................ 1055/93

[51] Int. Cl.$^6$ ..................... C07D 401/14; A61K 31/44
[52] U.S. Cl. ..................... 514/338; 514/394; 514/333; 514/307; 514/314; 546/70; 546/256; 546/167; 546/144; 546/304; 546/273.4; 546/269.4; 546/269.1; 548/126; 548/306.1; 548/305.4; 548/131; 548/302.1; 540/495; 540/494; 544/139
[58] Field of Search ..................... 546/271, 256; 548/306.1; 514/338, 397, 333

[56] References Cited

U.S. PATENT DOCUMENTS 5,158,969 10/1992 Olesen et al. .................... 514/419
5,360,809 11/1994 Axelsson et al. .................... 514/338

FOREIGN PATENT DOCUMENTS 0520200 12/1992 European Pat. Off. .
0563001A1 3/1993 European Pat. Off. .
0563001 9/1993 European Pat. Off. .

OTHER PUBLICATIONS

European Search Report for corresponding EPA 0616807A1–three (3) pages.
Chem. Abstracts, vol. 100, No. 17, abstract No. 139029t, Apr. 23, 1984, Hussein et al., "1–(para or meta–cinnamoylphenyl)–5–nitrobenzimidazoles", p. 644.
Potts et al., "Aromatic substitution by N–arylhydroxylamines–I", Tetrahedron, vo. 31, Sep. 1975, pp. 2163–2170.
J. Chem. Soc. (C), 1970, pp. 85–91; "Synthesis of Heterocyclic Compounds. Part II.$^1$ N—Arylazoles by Ullmann Condensation", by Khan and Polya.
Anathan et al., J. Med. Chem. 1993, 36, 479–490.
Fryer, R. I. Ligand Interactions at the Benzodiazepine Receptor. In "Comprehensive Medicinal Chemistry"; Hansch, C., Sammes, P. G. Taylor, J. B., Eds.; Pergamon Press: New York, 1990, vol. 3, pp. 539–541.
Maryanoff et al., J. Med. Chem. 1995, 38, 16–20.

*Primary Examiner*—Jane Fan
*Attorney, Agent, or Firm*—The Firm of Gordon W. Hueschen

[57] ABSTRACT

The present patent application discloses compounds having the formula

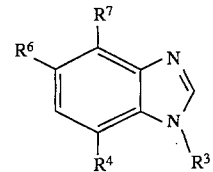

or a pharmaceutically acceptable salt thereof wherein $R^3$, $R^4$, $R^6$ and $R^7$ each have the meanings set forth in the specification.

The compounds are useful for the treatment of various central nervous system disorders such as epilepsy and other convulsive disorders, anxiety, sleep disorders and memory disorders.

6 Claims, No Drawings

BENZIMIDAZOLE COMPOUNDS

The present application is a division of application Ser. No. 8/207,774, filed Mar. 8, 1994, now abandoned.

This invention relates to novel benzimidazole compounds, pharmaceutical compositions thereof, a method of treating therewith, and to a method of preparing such benzimidazole compounds. The novel compounds are useful in the treatment of central nervous system diseases and disorders, and for example in the treatment of convulsions, anxiety, sleep disorders, and memory disorders.

BACKGROUND OF THE INVENTION

It is a well known fact, that specific sites in the central nervous system (the CNS) of a living animal body, including a human, exhibit highly specific binding for benzodiazepines such as for example diazepam. These binding sites are named benzodiazepine receptors. Lately, several subtypes of such benzodiazepine receptors have been isolated and described by techniques of modern molecular biology.

Numerous compounds belonging to different series of compounds having affinity for the benzodiazepine receptors have been synthesized during the last three decades. However, although the benzodiazepine receptor sites still are considered as very attractive biological sites for interfering with the CNS to treat various disorders and diseases, then nearly all previously synthesized compounds acting at these receptor sites have failed during clinical development because of unacceptable side effects.

Therefore, there is still a large need to identify novel compounds interacting with the benzodiazepine receptors.

OBJECT OF THE INVENTION

It is an object of the present invention to provide novel benzimidazole compounds and pharmaceutically-acceptable acid addition salts thereof, which are useful for the treatment of central nervous system disorders, diseases or ailments, and especially for the treatment of convulsions, anxiety, sleep disorders, and memory disorders.

Another object of the present invention is to provide parmaceutical compositions comprising the novel benzimidazole compounds being useful for above purposes.

Still another object of the present invention is to provide a novel method of treating with the novel benzimidazole compounds.

A further object of the present invention is to provide a method of preparing the novel benzimidazole compounds.

Additional objects will be obvious from the following description, and others will be obvious to one skilled in the art.

SUMMARY OF THE INVENTION

The invention then, inter alia, comprises the following, alone or in combination:

A compound having the formula:

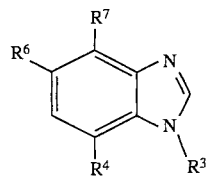

or a pharmaceutically acceptable salt thereof wherein $R^3$ is

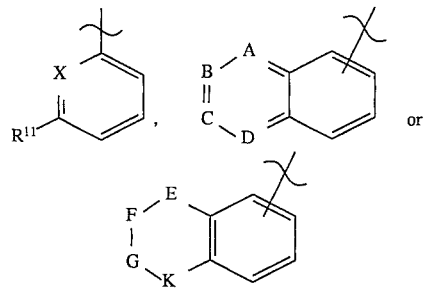

wherein

X is N; or C—R' wherein R' is hydrogen or together with $R^4$ forms a —$(NR^{111})_m$—C(=O)—, —$(NR^{111})_m$—CHOH—, or a —N=C— bridge wherein $R^{111}$ is hydrogen or alkyl and m is 0 or 1;

one of A, B, C, and D is N and the others are CH;

one of E, F, G, and K is N—R" wherein R" is hydrogen or alkyl and the others of E, F, G, and K are $CH_2$;

$R^6$ and $R^7$ are independently hydrogen; halogen; amino; nitro; cyano; acylamino; trifluoromethyl; alkyl; alkoxy; COO-alkyl; acyl; CH=NOH, CH=NO-alkyl; CH=N—NH—(C=O)—$NH_2$; phenyl which may be substituted one or more times with alkyl, nitro, halogen, or $CF_3$; or aryl which may be substituted one or more times with alkyl, phenyl, halogen, or $CF_3$; or $R^6$ and $R^7$ together forms a $(CH_2)_a$—$(Z)_b$—$(C=Y)_c$—$(Z')_d$—$(CH_2)_e$ bridge wherein each of Z and Z' independently are O, S, or NR'" wherein R'" is hydrogen or alkyl, Y is O or $H_2$, a and e are each independently 0, 1, 2, or 3 and b, c, and d are each independently 0 or 1 provided that the sum of a, b, c, d, and e is not larger than 6; Or $R^6$ and $R^7$ together forms a —CH=CH—CH=N—, —CH=CH—N=CH—, —CH=N—CH=CH—, —N=CH—CH=CH—, or =N—S—N= bridge;

$R^4$ is hydrogen; amino; nitro; cyano; halogen; acylamino; phenyl which may be substituted one or more times with alkyl, amino, halogen, or $CF_3$; aryl which may be substituted one or more times with alkyl, phenyl, halogen, or $CF_3$; or $R^4$ together with R' forms a —$(NR^{111})_m$—C(=O)—, —$(NR^{111})_m$—CHOH—, or a —N=C— bridge wherein $R^{111}$ is hydrogen or alkyl, and m is 1;

$R^{11}$ is phenyl which may be substituted one or more times with alkyl, halogen, or $CF_3$; benzimidazolyl which may be substituted one or more times with alkyl, halogen, or $CF_3$; or aryl which may be substituted one or more times with alkyl, phenyl, halogen, or $CF_3$, amino, nitro, cyano, acylamino, trifluoromethyl; alkoxy; or acyl; provided that at least one of $R^6$ and $R^7$ is other than hydrogen, and a compound as above wherein $R^4$ is hydrogen and $R^3$ is

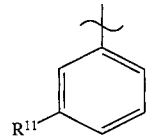

wherein $R^{11}$ is pyridyl, and
a compound as above, which is
1-[3-(3-pyridyl)-phenyl]-5-methylaldoximo-benzimidazole,
1-[3-(3-pyridyl)-phenyl]-5-1-propyl-benzimidazole,
1-[3-(3-pyridyl)-phenyl]-5-(2-furanyl)-benzimidazole, 1-[3-(3-pyridyl)-phenyl]-6-iodo-benzimidazole, 1-[3-(1-imidazolyl)-phenyl]-5-methyl-benzimidazole, 1-[3-(1-imidazolyl)-phenyl]-5-t-butyl-benzimidazole, 1-[3-(1-imidazolyl)-phenyl]-5-phenyl-benzimidazole, 1-[3-(1-imidazolyl)-phenyl]-5-i-propyl-benzimidazole, 1-[3-(3-pyridyl)-phenyl]-5-iodo-benzimidazole, 1-[3-(3-pyridyl)-phenyl]-5-t-butyl-benzimidazole, 1-[3-(1-benzimidazolyl)-phenyl]-5-i-propyl-benzimidazole, 1-[3-(1-(2-methylimidazolyl))-phenyl]-5-phenyl-benzimidazole, 1-[3-(1-benzimidazolyl)-phenyl]-5-trifluoromethyl-benzimidazole, 1-[3-(3-pyridyl)-phenyl]-5-(3-furanyl)-benzimidazole, or 4-trifluoromethyl-6,7-dihydro-6-methyl-7-oxo-benzimidazo[3,4-ab][1,4]benzodiazepine, or a pharmaceutically acceptable salt thereof, and a pharmaceutical composition comprising an effective amount of a compound as any above, or a pharmaceutically-acceptable addition salt thereof, together with at least one pharmaceutically-acceptable carrier or diluent, and a method of treating a disorder or disease of a living animal body which is responsive to modulation of the benzodiazepine receptor of the central nervous system of a living animal body, including a human, which comprises administering to such a living animal body, including a human, in need thereof a therapeutically-effective amount of a compound selected from those having the formula:

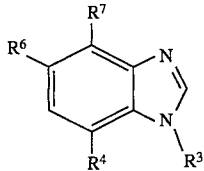

or a pharmaceutically acceptable salt thereof wherein $R^3$ is

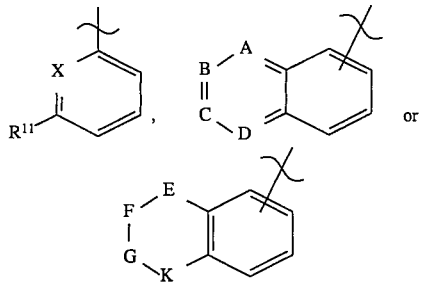

wherein

X is N; or C—R' wherein R' is hydrogen or together with $R^4$ forms a —$(NR^{111})_m$—C(=O)—, —$(NR^{111})_m$—CHOH—, or a —N=C— bridge wherein $R^{111}$ is hydrogen or alkyl and m is 0 or 1;

one of A, B, C, and D is N and the others are CH;

one of E, F, G, and K is N—R" wherein R" is hydrogen or alkyl and the others of E, F, G, and K are $CH_2$;

$R^6$ and $R^7$ are independently hydrogen; halogen; amino; nitro; cyano; acylamino; trifluoromethyl; alkyl; alkoxy; COO-alkyl; acyl; CH=NOH, CH=NO-alkyl; CH=N—NH—(C=O)—$NH_2$; phenyl which may be substituted one or more times with alkyl, nitro, halogen, or $CF_3$; or aryl which may be substituted one or more times with alkyl, phenyl, halogen, or $CF_3$; or $R^6$ and $R^7$ together forms a $(CH_2)_a$—$(Z)_b$—(C=Y)$_c$—$(Z')_d$—$(CH_2)_e$ bridge wherein each of Z and Z' independently are O, S, or NR''' wherein R''' is hydrogen or alkyl, Y is Q or $H_2$, a and e are each independently 0, 1, 2, or 3 and b, c, and d are each independently 0 or 1 provided that the sum of a, b, c, d, and e is not larger than 6; or $R^6$ and $R^7$ together forms a —CH=CH—CH=N—, —CH=CH—N=CH—, —CH=N—CH=CH—, —N=CH—CH=CH—, or =N—S—N= bridge;

$R^4$ is hydrogen; amino; nitro; cyano; halogen; acylamino; phenyl which may be substituted one or more times with alkyl, amino, halogen, or $CF_3$; aryl which may be substituted one or more times with alkyl, phenyl, halogen, or $CF_3$; or $R^4$ together with R' forms a —$(NR^{111})_m$—C(=O)—, —$(NR^{111})_m$—CHOH—, or a —N=C— bridge wherein $R^{111}$ is hydrogen or alkyl, and m is 1;

$R^{11}$ is halogen; amino; nitro; cyano; COO-alkyl; acylamino; $CF_3$; alkyl; alkoxy; morpholinyl; phenyl which may be substituted one or more times with alkyl, halogen, or $CF_3$; benzimidazolyl which may be substituted one or more times with alkyl, halogen, or $CF_3$; or aryl which may be substituted one or more times with alkyl, phenyl, halogen, or $CF_3$, amino, nitro, cyano, acylamino, trifluoromethyl; alkoxy; or acyl, and a method as above, wherein $R^4$ is hydrogen and $R^3$ is

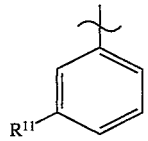

wherein $R^{11}$ is pyridyl, and a method as any above, wherein anxiety, sleep disorders, memory disorders, epilepsy or any other convulsive disorder is treated, and a method as above, wherein the compound employed is 1-[3-(3-pyridyl)-phenyl]-5-methylaldoximo-benzimidazole, 1-[3-(3-pyridyl)-phenyl]-5-i-propyl-benzimidazole, 1-[3-(3-pyridyl)-phenyl]-5-(2-furanyl)-benzimidazole, 1-[3-(3-pyridyl)-phenyl]-6-iodo-benzimidazole, 1-[3-(1-imidazolyl)-phenyl]-5-methyl-benzimidazole, 1-[3-(1-imidazolyl)-phenyl]-5-t-butyl-benzimidazole, 1-[3-(1-imidazolyl)-phenyl]-5-phenyl-benzimidazole, 1-[3-(1-imidazolyl)-phenyl]-5-i-propyl-benzimidazole, 1-[3-(3-pyridyl)-phenyl]-5-iodo-benzimidazole, 1-[3-(3-pyridyl)-phenyl]-5-t-butyl-benzimidazole, 1-[3-(1-benzimidazolyl)-phenyl]-5-i-propyl-benzimidazole, 1-[3-(1-(2-methylimidazolyl))-phenyl]-5-phenyl-benzimidazole, 1-[3-(1-benzimidazolyl)-phenyl]-5-trifluoromethyl-benzimidazole, 1-[3-(3-pyridyl)-phenyl]-5-(3-furanyl)-benzimidazole, or 1-trifluoromethyl-6,7-dihydro-6-methyl-7-oxo-benzimidazo[3,4-ab][1,4]benzodiazepine, or a pharmaceutically-acceptable addition salt thereof, and the method as any above, wherein the active ingredient is administered in form of a pharmaceutical composition thereof, in which it is present together with a pharmaceutically-acceptable carrier of diluent.

Halogen is fluorine, chlorine, bromine, or iodine.

Alkyl means a straight chain or branched chain of from one to eight carbon atoms or cyclic alkyl of from three to seven carbon atoms, including but not limited to, methyl, ethyl, propyl, isopropyl, butyl, isobutyl, t-butyl, pentyl, hexyl, cyclopropyl, cyclobutyl, cyclopentyl, cyclohexyl; methyl, ethyl, propyl, isopropyl and t-butyl are preferred groups.

Alkoxy means O-alkyl, wherein alkyl is as defined above.

Acyl means (C=O)—H or (C=O)-alkyl, wherein alkyl is as defined above.

Alkylene is an alkylene group of from one to eight carbon atoms which may be straight or branched.

Acylamino is acyl NH wherein acyl is as defined above.

Amino is $NH_2$ or NH-alkyl or N-(alkyl)$_2$, wherein alkyl is as defined above.

Aryl is a 5- or 6-membered heterocyclic monocyclic group. Such an aryi group includes, for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol- 3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol-4-yl, 1-imidazolyl, 2-imidazolyl, -imidazolyl, 5-imidazolyl, 2-pyrrolyl, 3-pyrrolyl, 2-furanyl, 3-furanyl, 2-thienyl, 3-thienyl, 2opyridyl, 3-pyridyl, 4-pyridyl.

Examples of pharmaceutically-acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate for example.

Other acids such as oxalic acid, while not in themselves pharmaceutically acceptable may be useful in the preparation of salts useful as intermediates in obtaining compounds of the invention and their pharmaceutically acceptable acid addition salts. Such salts are formed by procedures well known in the art.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention exist in (+) and (−) forms as well as in racemic forms. Racemic forms can be resolved into the optical antipodes by known methods, for example, by separation of diastereomeric salts thereof, with an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallization of d- or l- (tartrates, mandelates, or camphorsulphonate) salts for example. The compounds of the instant invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolution of optical isomers, known to those skilled in the art may be used, and will be apparent to the average skilled in the art. Such methods include those discussed by J. Jaques, A. Collet, and S. Wilen in "Enantiomers, Racemates, and Resolutions", John Wiley and Sons, New York (1981).

Starting materials for the processes described in the present application are known or can be prepared by known processes from commercially available chemicals.

The products of the reactions described herein are isolated by conventional means such as extraction, crystallization, distillation, chromatography, and the like.

Biology 4-aminobytyric acid (GABA) is the major inhibitory neurotransmitter and has been shown to act throughout both the central and peripheral nervous system. At present two types of GABA receptors are known, the $GABA_A$ and the $GABA_B$ receptors. Recent molecular biology has demonstrated that the $GABA_A$ receptors can be subdivided into numerous subreceptors consistant with the selective and or partial pharmacological effects observed with certain benzodiazepine receptor ligands as opposed to the unselective effects observed for the classical benzodiazepine receptor ligands such as for example diazepam. Activation of GABA receptors leads to alternations in membrane potential (hyperpolarization). The $GABA_A$ receptors are associated with chloride influx through its associated and integrated chloride channel, whereas GABAs receptor activation indirectly alters potassium and calcium channels as well as modifies second messenger production. The $GABA_A$ recognition sites can be activated by GABA, muscimol; and isoguvacine for example, but not by $GABA_B$ agonists such as for example baclofen. The modulatory $GABA_A$ recognition site at the benzodiazepine receptor sites can be selectively radiolabelled with $^3$H-fiunitrazepam. The affinity of various potential ligands for the benzodiazepine receptor sites can thus be evaluated by estimating the ability of test compounds to displace $^3$H-flunitrazepam.

Method

Tissue preparations are performed at zero to four degrees celcius. Cerebral cortex from male Wistar rats (150–200 g) is homogenized in 2 times 10 ml Tris-HCl, 30mM at pH 7.4 The resulting suspension is centrifuged at 40,000 g for 15 minutes. The pellet is washed three times with buffer, centrifuged at two degrees celcius at 40,000 g for ten minutes. The washed pellet is homogenized in 2 times 10 ml of buffer and is thereafter incubated on a water bath at 37° C. for 30 minutes and is thereafter centrifuged at 40,000 g for 10 minutes. The pellet is then homogenized with buffer and is centrifuged at 0° C. for 10 minutes at 40,000 g. The final pellet is resuspended in 30 ml buffer and the preparation may thereafter be stored at −20° C. In the test situation the membrane preparation is thawed and centrifuged at 2° C. for ten minutes at 48,000 g. The pellet is then washed two times with 2 times 10 ml 50 mM Tris-citrate at pH 7.1 using an UltraTurrax homogenizer and centrifuged at 48,000 g for 10 minutes. The hereby obtained pellet is resuspended in 50 mM Tris-citrate at pH 7.1,500 ml buffer per gram of original tissue, and is then used for binding assays. Aliquots of 0.5 ml tissue is added to 0.025 ml of 3H-flunitrazepam, final concentration of 1 nM, and is mixed and incubated for 40 minutes at 2° C. Non-specific binding is determined using clonazepam, at 100 ng/ml final concentration. After incubation 5 ml of icecold buffer is added to the samples and these are poured directly onto Whatman GF/C glass fibre filters under suction and is immediately washed with 5 ml icecold buffer. The amount of radioactivity on the filters is determined by conventional liquid scintillation counting. Specific binding is total binding minus non specific binding. Test value is calculated as the $IC_{50}$ which is equivalent to the concentration which inhibits the specific binding by 50 percent.

Test results obtained by testing selected compounds of the present invention appear from the following table:

TABLE

| Test compound: | $IC_{50}$ (nM) |
|---|---|
| 1-[3-(1-imidazolyl)-phenyl]-5-methyl-benzimidazole | 1.2 |
| 1-[3-(1-imidazolyl)-phenyl]-5-t-butyl-benzimidazole | 2.4 |
| 1-[3-(1-imidazolyl)-phenyl]-5-phenyl-benzimidazole | 7.4 |
| 1-[3-(1-imidazolyl)-phenyl]-5-i-propyl-benzimidazole | 0.6 |
| 1-[3-(3-pyridyl)-phenyl]-5-iodo-benzimidazole | 1.7 |
| 1-[3-(3-pyridyl)-phenyl]-5-t-butyl-benzimidazole | 10 |
| 1-[3-(1-benzimidazolyl)-phenyl]-5-i-propyl-benzimidazole | 4.3 |
| 1-[3-(1-(2-methylimidazolyl))-phenyl]-5-phenyl-benzimidazole | 9 |
| 1-[3-(1-benzimidazolyl)-phenyl]-5-trifluoromethyl-benzimidazole | 9.2 |
| 1-[3-(3-pyridyl)-phenyl]-5-(3-furanyl)-benzimidazole | 1.2 |
| 4-trifluoromethyl-6,7-dihydro-6-methyl-7-oxo-benzimidazo-[3,4-ab][1,4]benzodiazepine | 5.4 |

Pharmaceutical Compositions

While it is possible that, for use in therapy, a compound of the invention may be administered as the raw chemical, then it is preferable to present the active ingredient as a pharmaceutical formulation.

The invention thus further provides a pharmaceutical formulation comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal ,and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing one (1) milligram of active ingredient or, more broadly, 0.01 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water propylene glycol solutions. For example, parenteral injection liquid preparations can be formulated in solutions in aqueous polyethylene glycol solution.

The compounds according to the present invention may thus be formulated for parenteral administration (e.g. by injection, for example bolus injection or continuous infusion) and may be presented in unit dose form in ampoules, prefilled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alter, natively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasel cavity by conventional means, for example with a dropper, pipette or spray. The formulations may be provided in single or multidose form. In the latter case of a dropper or pipette this may be achieved by the patient administering an appropriate, predetermined volume of the solution or suspension. In the case of a spray this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatin or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of this invention are extremely useful in the treatment of disorders or diseases of a living animal body due to their potent benzodiazepine receptor affinity. These properties make the compounds of this invention extremely useful in the treatment of convulsions, anxiety, sleep disorders, memory disorders as well as other disorders sensitive to benzodiazepine receptor binding activity. The compounds of this invention may accordingly be administered to a subject, including a human, in need of treatment, alleviation, or elimination of a disorder or disease associated with the benzodiazepine receptors. This includes especially convulsions, anxiety, sleep disorders and memory disorders.

Suitable dosage range are 0.01–100 milligrams daily, 0.1–50 milligrams daily, and especially 0.1–30 milligrams daily, dependent as usual upon the exact mode of administration, form in which administered, the indication toward which the administration is directed, the subject involved and the body weight of the subject involved, and further the preference and experience of the physician or veterinarian in charge.

The following examples in the form of examples, methods and in the form of tables according to which compounds of the invention have been prepared will illustrate the invention further; however they are not to be construed as limiting.

EXAMPLE 1

1-(3-idophenyl)-5-trifiuoromethylbenzimidazole (1a). A mixture of 2-amino-3'-iodo- 4-trifluoromethyldiphenylamine (1b) (6.00 g, 14.4 mmol) and formic acid (60 ml) was refluxed for 16 h. After evaporation to dryness, the remanence was dissolved in ethyl acetate (100 ml) and washed with water (100 ml). The organic phase was dried and evaporated. The crude product was purified by column chromatography with methylene chloride as the eluent. Yield 4.2 g, mp 86°–87° C.

EXAMPLE 2

1-(3-(1-imidazolyl)-phenyl)-5-trifluoromethylbenzimidazole (3a). A mixture of 1a (1.0 g, 2.58 mmol), imidazole (0.19 g, 2.73 mmol), potassium carbonate (0.38 g, 2.78 mmol), CuBr (20 mg, 0.15 mmol), and 1-methyl-2-pyrrolidone (5 ml) was heated to 200° C. for 18 hours. Dilution with water and extractive workup with ethyl acetate was followed by chromatography on silica gel. Yield: 0.43 g, mp. 177°–180° C.

EXAMPLE 3

2-Amino-3'-iodo-4-trifluoromethyldiphenylamine hydrochloride (1b). A mixture of 1c (6.0 g, 14.7 mmol), sodium sulfide nonahydrate (9.8 g, 44 mmol), ammonium chloride (2.35 g, 44 mmol), and 99% ethanol(100 ml) was refluxed under nitrogen for 3 hours. After cooling to room temperature the reaction mixture was poured into water (400 ml) and extracted with ethyl acetate. The organic phase was washed with water, dried and concentrated. The remanence was purified by column chromatography. The product was converted to the hydrochloride by addition of methanolic hydrogen chloride to the eluate followed by evaporation of the solvent. Yield 6.0 g, mp. 182°–185° C.

EXAMPLE 3a

Identical to Example 3 except for the products being isolated as the free bases.

EXAMPLE 4

2-amino-3'-(1-imidazolyl)-4-1-propyldiphenylamine hydrochloride (14b). A mixture of 14c (1 g, 3.11 mmol) and palladium on activated carbon (5%, 0. 1 g) in MeOH (25 ml) was hydrogenated at ambient pressure until the hydrogen uptake had ceased. The reaction mixture was filtered through celite into a few milliliters of etheral hydrogen chloride. Evaporation of solvent left 14b (0.95 g, 2.89 mmol). Mp. 185°–190° C.

EXAMPLE 4a

Identical to Example 4 except for the products being isolated as the free bases.

EXAMPLE 5

3'-Iodo-2-nitro-4-trifluoromethyldiphenylamine (1c), To a mixture of 3-iodoaniline (11.0 g, 50 mmol) and 4-chloro-3-nitrobenzotrifluoride (11.3 g, 50 mmol) in dry DMF (50 ml) under nitrogen, was added sodium hydride (2.55 g, 85 mmol) in small portions over 0.5 hours. The reaction mixture was stirred at room temperature for 12 hours. The mixture was poured into water (200 ml). Diethyl ether (300 ml) was added and the phases were separated. The etheral phase was washed with water (3×200 ml), dried and evaporated. The crude product was purified by column chromatography using petroleum ether/methylenechloride (4:1) as the eluent. The crystalline product was triturated with petroleum ether and filtered. Yield 12.6 g, mp. 98°–101° C.

EXAMPLE 5a

As Example 5 but with dry potassium carbonate as the base and a reaction temperature of 120° C.

EXAMPLE 6

3'-Bromo-4-t-butyl-2-nitrodiphenylamine (6d). 4-t-Butyl-2-nitroaniline (see Example 7) (2 g, 10.31 mmol), 3-bromo-1-iodobenzene (5.84 g, 20.62 mmol), potassium carbonate (1.52 g, 11 mmol) and Cu-bronze (20 mg) were thoroughly mixed and heated to 160° C. overnight. After cooling the reaction mixture was partitioned between water and toluene. The organic phase was dried with MgSO$_4$ and evaporated. The remanence was passed through a silica gel column with ethyl acetate/petroleum ether (1:9) as the eluent to yield 6d (2.27 g, 61%). Mp 86°–87° C.

EXAMPLE 7

4-t-Butyl-2-nitroaniline. 4-t-Butylaniline (5 g, 33.58 mmol) in acetic anhydride (25 ml) was stirred at ambient temperature for 0.5 h. The mixture was cooled in an ice-bath and nitric acid (6 ml, 65%) was added at such a rate that the temperature did not exceed 18° C. Following the addition the mixture was poured on ice (200 g). The precipitate was filtered off, washed thoroughly with water and dried to yield N-acetyl-4-t-butyl-2-nitroaniline (7.15 g, 90%). Mp. 109°–110° C.

This product (7 g, 29.66 mmol) was heated to reflux in sulfuric acid (30 ml, 70%) for 0.5 h. After cooling water (100 ml) was added. The product was filtered off, washed with water and air-dried to yield 4-t-butyl-2-nitroaniline (5.4 g, 94%). Mp. 107°–108° C.

EXAMPLE 8

4-ACetaminobipheny/-4-Aminobiphenyl (15 g, 88.76 mmol) in toluene (250 ml) was added acetic anhydride (8.5 ml, 90 mmol). The mixture was stirred at ambient temperature for 1 hour. Following the reaction the mixture was poured into petroleum ether (500 ml), the product was filtered off, washed with petroleum ether and dried to yield 4-acetaminobiphenyl (18.7 g).

4-Acetamino-3-nitrobiphenyl. 4-Acetaminobiphenyl (17 g, 80.57 mmol)in glacial acetic acid (600 ml) was added a solution of potassium nitrate (18 g, 178 mmol) in conc. sulphuric acid (75 ml) at such a rate that the temperature was kept below 30° C. Following the addition the mixture was stirred at ambient temperature for 72 hours. The reaction mixture was poured into ice-water (1200 ml). The product was filtered off, washed thoroughly with water and dried. Recrystallization from EtOH (99%, 150 ml) afforded 4-acetamino-3-nitrobiphenyl (8.7 g).

4-Amino-3-nitrobiphenyl. A mixture of N-acetyl-4-amino-3-nitrobiphenyl (8.5 g, 33.2 mmol), aqueous sodium hydroxide (100 ml, 1M) and dimethoxyethane (75 ml) was stirred at ambient temperature overnight. The mixture was poured into water (300 ml). The product was filtered off, washed with water and dried to yield 4-amino-3-nitrobiphenyl (7 g, 32.7 mmol). Mp. 157°–159° C.

EXAMPLE 9

2.6-Dinitro-4-trifluoromethyldiphenylamine (4k). 4-Chloro-3,5-dinitrobenzoetrifluoride (5 g, 18.5 mmol) in DMF (25 ml) was added aniline (3.7 ml, 40 mmol) at 5° C. The mixture was allowed to warm to room temperature. After complete reaction the mixture was poured into water (100 ml). The product was filtered off, washed with water and dried to yield the orange crystalline product. Yield 6.9 g. Mp 118°–120° C.

2-Amino-6-nitro-4-trifluoromethyldiphenylamine (4j). From 4k as described in Example 3. Mp 140°–143° C.

7-Nitro-1-phenyl-5-trifluoromethylbenzimidazole (4i). From 4j as described in Example 1. Mp 95°–98° C.

7-Amino-1-phenyl-5-trifluoromethylbenzimidazole hydrochloride(4 h). From 4i as described in Example 4.

7-Iodo-1-phenyl-5-trifluoromethylbenzimidazole (4 g). To a cooled suspension of 4h (4.8 g, 15 mmol) in a mixture of water (12 ml) and conc. hydrochloric acid (20 ml) was added a solution of sodium nitrite (1.2 g, 17 mmol in 5 ml water) at such a rate that the temperature was kept below 5° C. Following the addition the mixture was stirred for 10min. and a solution of potassium iodide (4 g, 24 mmol in 10 ml water) was added carefully. The mixture was left at ambient temperature until the evolution of nitrogen had ceased (approx. 2 h). Aqueous sodium sulphite was added and the product was filtered off. Purification was achieved by column chromatography on silica gel using a mixture of ethyl acetate and petroleum ether (1:9) as the eluent. Yield 1.3 g. Mp 118°–120° C.

EXAMPLE 10

5-Amino-1-(3-(3-pyridyl)phenyl)benzimidazole (19a). 24a (1 g, 3.16 mmol) in conc. hydrochloric acid (10 ml) was added tin(11)chloride (1.98 g, 10.43 mmol) and was refluxed overnight. After cooling the mixture was poured into water (50 ml). Following filtration the flitrate was cooled in an ice-bath and rendered alkaline by addition of 12M sodium hydroxide. A small volume of ethanol was added and the mixture was stirred at 0° C. until a homogeneous suspension was obtained. The product was filtered off, washed with water and air-dried. Yield 0.9 g. Mp 172°–175° C.

EXAMPLE 11

1-(3-(3'-Amino)biphenylyl)-5-t-butylbezimidazole (20a). 43a (1 g, 3.04 mmol), sodium bicarbonate (1.28 g, 15.2 mmol), 3-aminophenylboronic acid and tetrakis(triphenylphosphine)palladium (30 mg) was added to a mixture of water (10 ml) and dimethoxyethane (20 ml) under a stream of nitrogen. The reaction mixture was heated to 80° C. overnight, cooled to room temperature and poured into water (100 ml). A small volume of ethyl acetate was added and the mixture was stirred until the product had precipitated. Filtration and column chromatography on silica gel using ethyl acetate/petroleum ether (1:9) as the eluent yielded 20a (0.52 g. Mp 162°–164° C.).

EXAMPLE 12

1-(3-Bromophenyl)-5-dimethylaminobenzimidazole hydrochloride (23a). 25a (0.8 g, 2.78 mmol) in DMF (10 ml) was added potassium carbonate (0.83 g, 6 mmol) and iodomethane (0.36 ml, 5.83 mmol) and was stirred at ambient temperature for 4 hours. The mixture was poured into water (80 ml) and extracted with ethyl acetate. The organic phase was dried over $MgSO_4$, concentrated to a small volume and eluted through silica gel with ethyl acetate/petroleum ether (1:9). The solvent was evaporated and the oily product was dissolved in dry diethyl ether and precipitated as the hydrochloride on addition of etheral hydrochloric acid (2M). The product was filtered off and dried under nitrogen. Yield 0.21 g. Mp 146°–150° C.

EXAMPLE 13

5-t-Butyl-1-(5-(3-(2-pyridyl)oxadiazolyl))benzimidazole (26a). 44a (0.75 g, 2.55 mmol) in THF (30 ml) was heated to reflux. Carbonyldiimidazole (0.75 g, 4.5 mmol) was added and reflux was maintained for 1 hour. To 10 ml of this solution pyridin-2-carbamidoxime (0.28, 2 mmol) was added and the mixture was heated to reflux for 2 hours. After evaporation of the solvent, toluene (5 ml) was added and the mixture was refluxed overnight. Removal of solvent left a crude product which precipitated upon trituration with water. The product was filtered off, dried and washed with petroleum ether. Yield 0.29 g. Mp 139°–141 ° C.

Compounds 27a–30a and 33a were prepared analogueously from the appropiate carbamidoximes.

EXAMPLE 14

3-(4-Morpholinyl)nitrobenzene. 3-Nitroaniline (10 g, 72 mmol)in DMF (100 ml) was added bis(2-chloroethyl) ether (11.7 ml, 100 mmol) and potassium carbonate (27.6 g, 200 mmol). The mixture was heated to reflux for 10 hours. Additional bis(2-chloroethyl) ether (3 ml) was added and reflux was maintained for 18 hours. Addition of bis(2-chloroethyl) ether was repeated and reflux was continued for 4 hours. The solvent was evaporated and the residue partitioned between water and ethyl acetate. The organic phase was dried and evaporated. The residue was extracted with diethyl ether. The extract was concentrated and purified by column chromatography on silica gel with ethyl acetate/petroleum ether (3:7) as the eluent. Yield 3.4 g. Mp 87°–90° C.

3-(4-Morpholinyl)aniline. 3-(4-Morpholinyl)nitrobenzene (1.9 g, 9.1 mmol) was hydrogenated as described in Example 4. Yield 1.27 g. Mp 115° C. 4-t-Butyl-3'-(4-morpholinyl)-2-nitrodiphenylamine (32c). 4-t-Butyl-1-iodo-2nitrobenzene* (3 g, 10 mmol), 3-(4-morpholinyl)aniline (1.2 g, 6.7 mmol), potassium carbonate (1.38 g, 10 mmol) and Cu-bronze (30 mg) was thoroughly mixed and heated to 170° C. for 5 hours. The product was isolated and purified as described in Example 6. Yield 0.2 g oily product.

* 4-t-Butyl-l-iodo-2-nitrobenzene was prepared from 4-t-butyl-2-nitroaniline (Example 7) in analogy with 4 g (Example 9).

EXAMPLE 15

N,N'-Bis(2-nitro-4-trifluoromethyl)-1,3-phenylenediamine (42c) and N-(2-nitro-4-trifluoromethyl)-1,3-phenylenediamine (45c). 4-Chloro-2-nitrobenzoetrifluoride (7.6 ml, 50 mmol) in dry DMF was added triethyl amine (7 ml, 50 mmol) and 1,3phenylenediamine (3.24 g, 30 mmol). The mixture was heated to 80° C. overnight and then to 120° C. for 6 hours. The solvent was evaporated and the residue was partitioned between water and diethyl ether. The organic phase was dried and concentrated and-the product mixture was separated by column chromatography on silica gel using diethyl ether/petroleum ether (1:1) as the eluent. Yield of 42c: 3.7 g, mp 133°–135° C. Yield of 45c: 3.7 g, mp 110°–112° C.

N-(2-Nitrophenyl)- N'-(2-nitro-4-trifluoromethylphenyl)-1.3-phenylenediamine (39c). 45c (2 g, 6.7 mmol), 1-fluoro-2-nitrobenzene and potassium carbonate (1 g, 7 mmol) were thoroughly mixed and heated to 180° C. for 3 days. After cooling the reaction mixture was partitioned between water and ethyl acetate. The organic phase was dried, concentrated and extracted with diethyl ether. The etheral extract was passed through a short silica gel column to yield 39c, 0.8 g. Mp 95°–98° C.

EXAMPLE 16

N-(Acetyl)-.N'-(2-nitro-4-trifluoromethyl)-1,3-phenylenediamine (40c). 45c (1.7 g, 5.7 mmol) and triethyl amine (0.84 ml, 6 mmol) in THF (20 ml) was added acetylchloride (0.4 ml, 6 mmol). Following the addition water was added and the mixture was allowed to stir for 15min. The product was filtered off and air-dried. Mp 188°–190° C.

EXAMPLE 17

4-t-Butyl-3'-carboxy-2-nitrodiphenylamine (44c). 4-t-Butyl-2-nitroaniline (see Example 7), 3-iodobenzoic acid (10 g, 40 mmol), potassium carbonate (5.5 g, 40 mmol) and a catalytic amount of CuI were thoroughly mixed and heated to 230° C. for 4 hours. The reaction mixture was allowed to cool to 100° C. and water was added. After cooling to room temperature the solution was rendered acidic by careful addition of glacial acetic acid. The precipitate was filtered off and washed with dichloromethane. Recrystallization from 2-propanol afforded 44c. Yield 4.3 g. Mp 194°–195° C.

EXAMPLE 18

3-Acetyl-1,2-phenylendiamine hydrochloride was prepared from 3-acetyl-2-nitroaniline as described in Example 4. Mp 246°–250° C.

4-Acetylbenzimidazole was prepared from 3-acetyl-1,2-phenylendiamine as described in Example 1. Mp 220°–223° C.

4-Acetyl-1-(3-nitrophenyl)benzimidazole (3g). 4-Acetylbenzimidazole (4.4 g, 27.5 mmol) was dissolved in dry DMSO (40 ml) and cooled. Sodium hydride (0.91 g, 80% suspension in oil) was added and the mixture was allowed to warm to room temperature. When the evolution of hydrogen had ceased 1-fluoro-3-nitrobenzene was added and the mixture was heated to 120° C. overnight. After cooling the reaction mixture was poured into ice-water and the crude product was filtered off. Purification was achieved by column chromatography on silica gel with ethyl acetate/petroleum ether (1:1) as the eluent. Yield 2.09 g, mp 175°–177° C.

EXAMPLE 19

4-Nitrobenzimidazole was prepared from 3-nitro-1,2-phenylendiamine as described in Example 1. Mp 242°–245° C.

4-Nitro-1-(3-nitrophenyl)benzimidazole was prepared analogueously to 3 g from 4-nitrobenzimidazole and 1-fluoro-3-nitrobenzene. Mp 260°–262° C.

1-(3-Aminophenyl)-4,nitrobenzimidazole was prepared from 4-nitro-1-(3-nitrophenyl)benzimidazole as described in Example 3a. Mp 159°–161° C.

4-Nitro-1-(3-pivaloylaminophenyl)benzimidazole (5 g). 1-(3-Aminophenyl)-4-nitrobenzimidazol (0.15 g, 0.6 mmol) was suspended in THF (4 ml). Triethyl amine (0.084 ml, 0.6 mmol) and pivaloylchloride (0.074 ml, 0.6 ml in 1 ml THF) was added. After stirring for 3 hours at room temperature another equivalent of pivaloylchloride was added and the temperature was raised to 70° C. for 0.5 hours. After evaporation of solvent the residue was extracted with ethyl acetate. The extract was dried over MgSO4 and the solvent was removed by evaporation. Trituration with petroleum ether containing a few percent dichloromethane afforded 5g. Yield 0.12 g, mp 105°–110° C.

EXAMPLE 20

4-t-Butyl-1-fluorobenzene. 4-t-Butylaniline (14.9 g, 100 mmol) was suspended in aqueous hydrochloric acid (50 ml, 6M) at 5° C. Sodium nitrite (7.6 g, 110 mmol in 10 ml water) was added at such a rate that the temperature was kept between 5°–7° C. Following the addition the resulting solution was stirred for 15 min. and sodium tetrafluoroborate (15.4 g, 140 mmol in 30 ml water) was added at 5–8° C. The mixture was stirred for 15 min. 4-t-Butylbenzenediazonium tetrafluoroborate was filtered off, dried with suction and washed with diethyl ether to yield 20.96 g. This diazonium salt was decomposed by heating to 140° C. on an oil-bath. The product was distilled off at reduced pressure. Yield 11.15 g colorless oil.

4-t-Butyl-1-fluoro-2-nitrobenzene. 1-Fluoro-4-t-butylbenzene (10 g, 65.79 mmol) was dissolved in concentrated sulfuric acid (40 ml) at 0° C. Solid potassium nitrate (6.64 g, 65.79 mmol) was added in small portions during 1 hour. The temperature was kept below 5° C. Following the addition stirring was continued for 2 hours. The reaction mixture was poured into ice-water (400 ml) and extracted with dichloromethane (3×50 ml). The organic phase was washed with water, aqueous sodium bicarbonate (1 M) and water successively, dried over MgSO$_4$ and filtered through silica gel (5 g). Evaporation of solvent left the crude product (10.32 g). Column chromatography on silica gel using petroleum ether containing 1% dichloromethane as the eluent afforded the pure product (7.6 g colorless oil).

N-(2-Bromo-6-pyridyl)-4-t-butyl-2-nitroaniline. 4-t-Butyl-1-fluoro-2-nitrobenzene (1.97 g, 10 mmol), 2-amino-6-bromopyridine (1.73 g, 10 mmol) and potassium carbonate (1.38 g, 10 mmol) were thoroughly mixed and heated to 150° C. overnight. The temperature was raised to 180° C. for 30 hours. After cooling water and a small amount of ethyl acetate was added and the mixture was stirred for 1 hour. The organic phase was dried and concentrated and eluted through silica gel with petroleum ether/diethyl ether (9:1). Yield: 1.25 g, mp 78°–81° C.

2-Amino-N-(2-bromo-6-pyridyl)-4-t-butylaniline was prepared from N-(2-bromo- 6-pyridyl)-4-t-butyl-2-nitroaniline (1.25 g, 3.57 mmol) as described in Example 3. Yield: 0.85 g, mp 125°–128° C.

1-(2-Bromo-6-pyridyl)-5-t-butylbenzimidazole (6 g) was prepared from 2-Amino-N-( 2-bromo-5-pyridyl)-4-t-butylaniline (0.8 g) as described in Example 1. Yield: 10 mg*, mp 98°–100° C.

*Most of the starting material was formulated without ring-closure.

EXAMPLE 21

1-(3-Bromophenyl)-4-nitrobenzimidazole (7 g). 4-Nitrobenzimidazole (see Example 19. 0.75 g, 4.6 mmol), 1,3-dibromobenzene (1.11 ml, 9.2 mmol), potassium carbonate (0.64 g, 4.6 mmol) and a catalytic amount of Cu-bronze were mixed in dry 1-methyl-2-pyrrolidone (2 ml) and heated to 140° C. for 3 days. One equivalent of 1,3-dibromobenzene was added and heating was continued for 24 hours. The cooled reaction mixture was extracted with ethyl acetate. The extract was dried and concentrated and eluted through silica gel with ethyl acetate/methanol (9:1) to yield 7g (33 mg, mp 180°–182° C.).

EXAMPLE 22

Ethyl N-(2,6-dinitro-4-trifluoromethylphenyl)anthranilate (1i). To a mixture of 4-chloro- 3,5-dinitrobenzoetrifluoride (6.76 g, 25 mmol) and ethyl anthranilate (3.7 ml, 25 mmol) in dry DMF (20 ml) was added sodium hydride (30 mmol, 1.2 g 60% suspension in oil) in small portions. The mixture was stirred at 80° C. overnight, cooled and poured into ice-water (400 ml). The product was filtered off, washed with water and dried. Recrystallization from ethanol (200mi) yielded 1i (7.27 g, mp 152°–154° C.).

1j, 1i (3.42 g, 8.56 mmol) and ammonium chloride (1.37 g, 25.7 mmol) in ethanol (50 ml) was added a solution of sodium sulfide nonahydrat (6.17 g, 25.7 mmol in 50 ml ethanol) at 0° C. The mixture was allowed to heat to room temperature. After 1 hour the mixture was filtered and the flitrate was evaporated to dryness. Trituration of the residue with ethyl acetate/petroleum ether (1:9) and diethyl ether successively afforded 1j. Yield: 2.28 g, mp 285°–293° C.

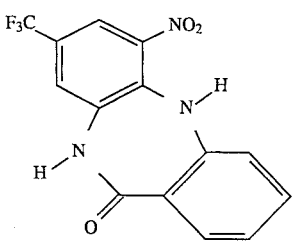

1h, 1j (1.43 g, 4.42 mmol) was hydrogenated as described in Example 4. The product was isolated as the free base. Yield: 0.66 g.

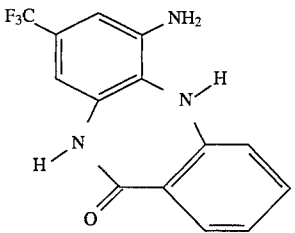

1f (see Table 5 for structure) was prepared from 1h (0.66 g, 2.24 mmol) as described in Example 1. Yield: 0.42 g, mp 330°–332° C.

EXAMPLE 23

2f (see Table 5 for structure)If (1g, 3.3 mmol) in dry DMF (10 ml) was added sodium hydride (0.1 g, 3.3 mmol) at 0° C. Following the addition the mixture was stirred at ambient temperature for 20min. Iodomethane (0.52 g, 3.66 mmol) was added and stirring was continued for 4 hours. The reaction mixture was poured into water (40 ml), the product was filtered off and dried. Trituration with dry diethyl ether yielded 2f (0.37 g, mp 197°–198° C.).

EXAMPLE 24

4f (see Table 5 for structure). 2f (0.1 g, 0.33 mmol) in dry THF (4 ml) was added LiAlH$_4$ (10 mg, 0.33 mmol) at 0° C. The reaction mixture was stirred for 15 min. and poured into ice-water (10 ml). The product was filtered off and dried to yield 4f (0.1 g, mp 169°–170° C.).

EXAMPLE 25

2',6'-Dinitro-2-hydroxymethyl-4'-trifluoromethyldiphenylamine (5j). A mixture of 4-chloro-3,5-dinitrobenzoetrifluoride (10 g, 36.96 mmol), 2-hydroxymethylaniline (5 g, 40.66 mmol) and potassium carbonate (5.1 g, 36.96 mmol) in DMF (250 ml) was stirred at ambient temperature for 1.5 hours. The reaction mixture was poured into ice-water (1 l) and the product was filtered off. Trituration with petroleum ether containing a small amount of dichloromethane afforded 5j (9.73 g, mp 117°–120° C.).

2',6'-Dinitro-2-(4-toluensulfonyloxymethyl)-4'-trifluoromethyldiphenylamine (5i). 5j (9 g, 25.19 mmol) in pyridine (55 ml) was added 4-toluenesulfonyl chloride in small portions at ambient temperature. Following the addition the mixture was stirred at 40° C. overnight, poured into ice-water and acidified with hydrochloric acid. The product was extracted with ethyl acetate and isolated by evaporation of the solvent. Trituration with diethyl ether afforded pure 5i. Yield 13.49 g.

5h, 5i (7 g, 13.69 mmol) and ammonium chloride (4.4 g, 82.12 mmol) in ethanol (250 ml) was added sodium sulfide (19.7 g, 82.12 mmol) in small portions at 0° C. Following the addition the mixture was stirred at ambient temperature for 5 hours. Filtration and evaporation of solvent left a crude product, which upon extraction with diethyl ether and column chromatography on silica gel using ethyl acetate/petroleum ether (1:1 ) as the eluent afforded pure 5h (1.51 g, mp 135°–138° C.):

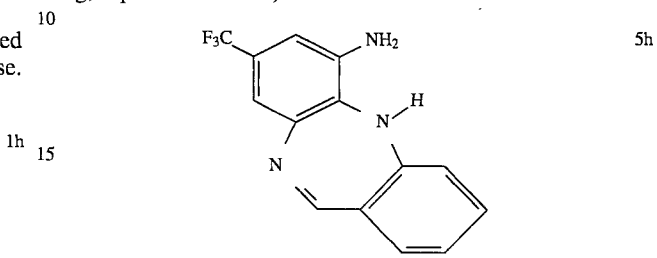

5f (see Table 5 for structure). 5 h (1.46 g, 5.23 mmol) was refluxed in formic acid (50 ml) for 1.5 hours. The cooled mixture was poured into water (200 ml) and extracted with ethyl acetate. The extract was eluted through silica gel with ethyl acetate to yield a formulated product which upon reflux in methanolic sodium hydroxide afforded 5f. Yield 0.58 g, mp 242°–243° C.

EXAMPLE 26

N-(4-Methyl-2-nitrophenyl)anthranilic acid (6j). 2-iodobenzoic acid (5 g, 20.16 mmol), 4-methyl-2-nitroaniline (6.12 g, 40.32 mmol), potassium carbonate (2.8 g, 20.3 mmol) and CuI (0.2 g) were thoroughly mixed and heated to 200° C. for 1 hour. After cooling the solid reaction mixture was partitioned between ethyl acetate and aqueous sodium hydroxide (1M). The product precipitated from the aqueous phase on acidification with hydrochloric acid (4M). Yield 3.69 g, mp 209°–213° C.

9,10-Dihydro-2-methyl-4-nitroacredin-9-one (6i). 6j (2.56 g, 9.41 mmol) was heated to 100° C. in conc. sulfuric acid (6 ml) for 1 hour. After cooling the mixture was poured into ice-water (50 ml). The product was filtered off, washed with water and air-dried. Quantitative yield, mp 232°–234° C.

9,10-Dihydro-4-amino-2-methylacredin-9-one (6 h) was prepared from 6i (2 g, 7.87 mmol) as described in Example 3. Yield 1.4 g, mp 292°–297° C.

6f (see Table 5 for structure) was prepared from 6 h (1 g, 4.46 mmol) as described in Example 1. Yield after recrystallization from ethanol: 0.4 g, mp 255°–257° C.

EXAMPLE 27

Imidazolo[6,7-d]phthalide (3h) was prepared from 6,7-diaminophthalide (3.7 g, 22.57 mmol) as described in Example 1. Yield 3.8 g, mp 280° C.

6-(3-nitrophenyl)imidazolo.[6,7-d]phthalide (3e). 3h (0.45 g, 2.5 mmol)in dry DMSO was added sodium hydride (0. 1 g 80% suspension in oil). After the evolution of nitrogen had ceased 3-fluoronitrobenzene (0.32 ml, 3 mmol) was added and the mixture was stirred at 120° C. for 2 days. After cooling water and a few drops of glacial acetic acid was added. The product was filtered off and purified by column chromatography on silica gel using dichloromethane/aceton (9:1) as the eluent. Yield 9 mg, Mp 266°–268° C.

EXAMPLE 28

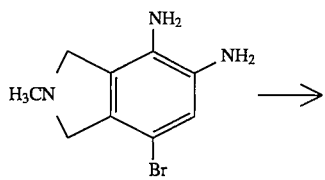

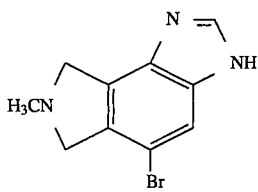

5-bromo-6,8-dihydro-7-methyl-2H-pyrrolo[3,4-e]benzimidazole.

A solution of 7-bromo-2,3-dihydro-2-methyl-1H-isoindole (0.6 g) in formic acid (10 ml) was refluxed for 5 hours, whereafter it was evaporated to dryness. The residue was treated with a mixture of water/EtOAc (5/5 ml). pH was adjusted to 9 with sodium carbonate, whereby the title compound precipitated as pale crystals. Mp. 225°–227° C.

EXAMPLE 29

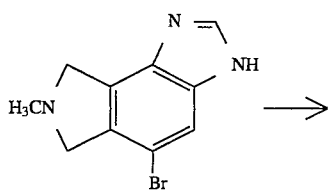

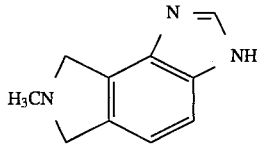

The above product was hydrogenated under standard conditions to give 2,3-dihydro- 2-methyl-1 H-isoindole hydrobromide with Pd/C as the catalyst. Mp. >300° C.

EXAMPLE 30

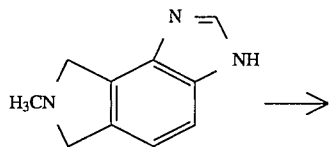

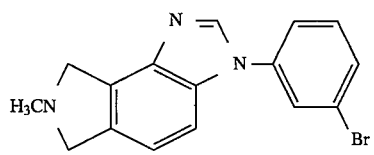

3-(3-bromophenyl)-6,8-dihydro-7-methyl-2H-pyrrolo[3,4-e]benzimidazole.

A mixture of 6,8-dihydro-7-methyl-2H-pyrrolo[3,4-e]benzimidazole (0.25 g), $K_2CO_3$ (0.26 g), 3-bromo-1-iodobenzene (0.8 g) and Copper powder (15–20 mg) was heated in N-methyl-2-pyrrolidone (5 ml) at 180° C. for 3 hours. The mixture was then partitioned between EtOAc and water. The organic phase was dried over $Na_2SO_4$ and evaporated. The oily residue was purified on $SiO_2$ with EtOAc as the eluent. $^1$H—NMR (500MHz,CDCl$_3$) ppm: 2.8(s,3H), 4.2(s,2H), 4.45(s,2H), 7.2–7.7(m,6H aromatic) 8.1 (s, 1H imidazole).

EXAMPLE 31

3-(3-Nitrophenyl)-benzo[e]benzimidazole (2k). To 3k (2.2 g, 13 mmol)in dry DMSO (30 ml) was added sodium hydride (0.43 g 80% in oil, 14.3 mmol) at 0° C. When evolution of hydrogen had ceased 3-fluoronitrobenzene (1.52 ml, 14.3 mmol) was added and the mixture was heated to 110–120° C. for 2 days. After cooling the mixture was diluted with 4 volumes of water and extracted with ethyl acetate. Drying and evaporation of solvent followed by trituration with ethanol left 2k as yellow crystals (1.49 g, 40%). Mp 136–138° C.

3-(3-Nitrophenyl)-pyrido[1,3e]benzimidazole (4k) was prepared analogueously from 5k (0.7 g, 4-.14 mmol). Yield 0.25 g (21%). Mp 219°–221° C.

3-(3-nitrophenyl)-7-methyl-piperido[3,4-e]benzimidazole hydrochloride (6k) was prepared analogueously from 7k (1.56 g, 7 mmol) using two equivalents of sodium hydride. Yield 70 mg (3%). Mp 266°–269° C.

EXAMPLE 32

1,2-Diaminonaphtalene hydrochloride was prepared analogueously to 2-methyl- 1,2,3,4-tetrahydroisoquinoline as described in U.S. patent application Ser. No. 08/124,770 of Sep. 24, 1993. Mp 223°–226° C.

5,6-Diaminoquinoline hydrochloride was prepared from 5-amino-6-nitroquinoline (1 g, 5.29 mmol) as described in Example 4. Yield 1.0 g (97%). Mp 214°–220° C.

EXAMPLE 33

1-(3-(3-pyridyl)phenyl)-5-hydroxymethylbenzimidazole (49a). 48a (3.5 g, 9.8 mmol) in dry THF (25 ml) was added LiAlH4 (0.36 g, 4.9 mmol) portionswise during 1 hour at 0° C. under $N_2$. Following the addition the mixture was stirred at ambient temperature overnight. The reaction mixture was diluted with water and extracted with ethyl acetate. The organic phase was dried with MgSO$_4$ and evaporated. The residue was eluted through silica gel with EtOH/MeOH mixture (9:1). Evaporation of solvent from the pure fractions left 49a. Yield 1.58 g (54%). Mp 183°–185° C.

EXAMPLE 34

1-(3-(3-pyridyl)phenyl)-5-formylbenzimidazole (50a). 49a (0.68 g, 2.26 mmol) in toluene (5 ml) was added benzeneseleninic acid (0.64 g, 3.39 mmol). The mixture was heated to 70° C. for 5 hours. After cooling the product was filtered off and washed with warm toluene and $CH_2Cl_2$ successively. Yield 0.58 g (86%). Mp 00°–202° C.

EXAMPLE 35

1-(3-(3-pyridyl)phenyl)-5-aldoximobenzimidazole (52a), 50a (0.25 g, 0.84 mmol) in abs. EtOH (10 ml) was added hydroxylamine hydrochloride (0.17 g, 2.48 mmol). The suspension was heated to 70° C. for 30 min. After cooling water was added. The product was filtered off, washed with water and air-dried to yield 52a (0.14 g, 53%). Mp 228°–230° C.

EXAMPLE 36

1-(3-(3-pyridyl)phenyl)-5-semicarbazonobenzimidazole (55a). Analogueously to 52a with addition of one equivalent pyridine to the reaction mixture. Yield 0.18 g (60%). Mp 275°–278° C.

EXAMPLE 37

1-Phenyl-5-trifluoromethyl-7-benzoylaminobenzimidazole (15 g). 14 g (0.3 g, 1.08 mmol) in THF (10 ml) was added triethylamine (0.3 ml) and benzoylchloride (0.23 ml). The mixture was stirred at ambient temperature overnight. The solvent was removed in vacuo and the remanence was partitioned between water and ethyl acetate. The organic phase was dried and evaporated. The oily residue was dissolved in diethyl ether, and the product precipitated upon addition of petroleum ether. Yield 0.15 g (36%). Mp 152°–155° C.

EXAMPLE 38

1-(3-Bromophenyl)-5-methoxymethylbenzimidazole (66a). 65a (1 g, 3.3 mmol) in dry DMF (10 ml) was added sodium hydride (0.11 g 80% in oil, 3.63 mmol) at 0° C. When evolution of hydrogen had ceased iodomethane (0.23 ml, 3.63 mmol) was added, and the mixture was stirred at 40° C. for 1 hour. Dilution with water and extractive workup with ethyl acetate followed by column chromatography on silica gel, using ethyl acetate as the eluent, afforded 66a as a colorless oil. Yield 0.52 g (59%).

TABLE 1

Compounds 1a–66a.

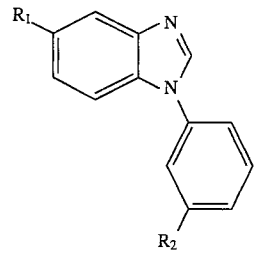

| No. | $R_1$ | $R_2$ | Mp/°C. | Starting material | Example |
|---|---|---|---|---|---|
| 1a | $CF_3$ | I | 86–87 | 1b | 1 |
| 2a | Me | CN | 142–143 | 2b | 1 |
| 3a | $CF_3$ | 1-imidazolyl | 177–180 | 1a | 2 |
| 4a | i-$PrO_2C$ | 1-imidazolyl | 125–128 | 4b | 1 |
| 5a | Me | 1-imidazolyl | 167–168 | 5b | 1 |
| 6a* | t-Bu | 1-imidazolyl | 200–210 | 6b | 1 |
| 7a | t-Bu | 1-(4-phenylimidazolyl) | 175–177 | 7b | 1 |
| 8a* | t-Bu | 1-(4-methylimidazolyl) | 215–225 | 8b | 1 |
| 9a | Ph | 1-imidazolyl | 163–164 | 9b | 1 |
| 10a | n-Bu | 1-imidazolyl | | 10b | 1 |
| 11a | n-Bu | 1-(4-phenylimidazolyl) | | 11b | 1 |
| 12a | n-Bu | 1-(2-methylimidazolyl) | | 12b | 1 |
| 13a* | $(CH_2)_5CH$ | 1-imidazolyl | 222–225 | 13b | 1 |
| 14a* | i-Pr | 1-imidazolyl | 208–212 | 14b | 1 |
| 15a | i-Pr | 1-(4-phenylimidazolyl) | 215–218 | 15b | 1 |
| 16a | i-Pr | 1-(2-methylimidazolyl) | | 16b | 1 |
| 17a | $NO_2$ | 1-benzimidazolyl | 237–240 | 31a | 2 |
| 18a | I | 3-pyridyl | 200–202 | 19a | 9 |
| 19a | $NH_2$ | 3-pyridyl | 172–175 | 24a | 10 |
| 20a | t-Bu | 3-aminophenyl | 162–164 | 43a | 11 |
| 21a | t-Bu | 3-furanyl | 118–120 | 43a | 11[b] |
| 22a | t-Bu | 3-pyridyl | 137–140 | 43a | 11[c] |
| 23a* | $NMe_2$ | Br | 146–150 | 25a | 12 |
| 24a | $NO_2$ | 3-pyridyl | 229–230 | 31a | 11[c] |
| 25a | $NH_2$ | Br | 140–142 | 31a | 10 |
| 26a | t-Bu | 5-(3-(2-pyridyl)oxadiazolyl) | 139–141 | 44a | 13 |
| 27a | t-Bu | 5-(3-(3-pyridyl)oxadiazolyl) | 138–143 | 44a | 13 |
| 28a | t-Bu | 5-(3-(4-pyridyl)oxadiazolyl) | 94–96 | 44a | 13 |
| 29a | t-Bu | 5-(3-(2-furanyl)oxadiazolyl) | 157–159 | 44a | 13 |
| 30a | t-Bu | 5-(3-cyclopropyl)oxadiazolyl) | 176–178 | 44a | 13 |
| 31a | $NO_2$ | Br | 187–189 | 31b | 1 |
| 32a | t-Bu | 4-morpholinyl | 141–143 | 32b | 1 |
| 33a | t-Bu | 5-(3-methyl)oxadiazolyl | 142–145 | 44a | 13 |
| 34a | i-Pr | 1-benzimidazolyl | 150–152 | 34b | 1 |
| 35a | t-Bu | 1-(5-t-butyl)benzimidazolyl | 263–265 | 35b | 1 |
| 36a | $NO_2$ | 1-imidazolyl | 232–234 | 31a | 2 |
| 37a | t-Bu | CN | 138–140 | 37b | 1 |
| 38a | Ph | 1-(2-methyl)imidazolyl | 192–194 | 9b | 1 |
| 39a | $CF_3$ | 1-benzimidazolyl | 275–279 | 39b | 1 |
| 40a* | $CF_3$ | 3-acetamino | 223–226 | 40b | 1 |
| 41a | HCONH | 1-imidazolyl | 234–235 | 41b | 1[d] |

TABLE 1-continued

Compounds 1a–66a.

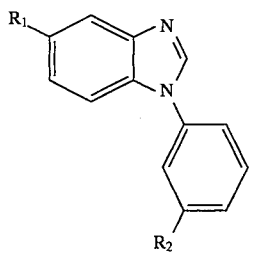

| No. | R₁ | R₂ | Mp/°C. | Starting material | Example |
|---|---|---|---|---|---|
| 42a | CF₃ | 1-(5-triflouromethyl)-benzimidazolyl | 171–172 | 42b | 1 |
| 43a | t-Bu | Br | 132–134 | 43b | 1 |
| 44a | t-Bu | COOH | 215–216 | 44b | 1 |
| 45a | 3-furanyl | 3-pyridyl | 160–163 | 18a | 11[b] |
| 46a | Ph | 3-pyridyl | 139–141 | 18a | 11[e] |
| 47a | i-PrO₂C | Br | 102–104 | 47b | 1 |
| 48a | i-PrO₂C | 3-pyridyl | 108–111 | 47a | 11[c] |
| 49a | CH₂OH | 3-pyridyl | 183–185 | 48a | 33 |
| 50a | CHO | 3-pyridyl | 200–202 | 49a | 34 |
| 51a | 3-pyridyl | 3-pyridyl | 178–182 | 18a | 11[c] |
| 52a | CHNOH | 3-pyridyl | 228–230 | 50a | 35 |
| 53a | 3-(3-cyclo-propyl)oxa-diazolyl | 3-pyridyl | 178–180 | 48a | 13 |
| 54a | 2-nitrophenyl | 3-pyridyl | 195–197 | 18a | 11[f] |
| 55a | CHNNH₂—C(O)NH₂ | 3-pyridyl | 275–278 | 50a | 36 |
| 56a | 1-imidazolyl | 3-pyridyl | 187–190 | 18a | 2 |
| 57a | 2-furanyl | 3-pyridyl | 160–165 | 18a | 2[g] |
| 58a | CH₂OCH₃ | 3-pyridyl | 119–120 | 66a | 11[e] |
| 59a | CHNOCH₃ | 3-pyridyl | 205–207 | 50a | 35[h] |
| 60a* | i-Pr | 3-pyridyl | 155–160 | 61a | 11[c] |
| 61a | i-Pr | Br | 82–86 | 61b | 1 |
| 62a* | cyclopropyl-methyloxy | Br | 160–168 | 63a | 38[i] |
| 63a | OH | Br | 230–234 | 63b | 1[j] |
| 64a | benzyloxy | Br | 189–193 | 63a | 33[k] |
| 65a | CH₂OH | Br | 112–114 | 47a | 33 |
| 66a | CH₂OCH₃ | Br | ** | 65a | 38 |

*isolated as the hydrochloride
**isolated as an oil
[a]decomp.
[b]Starting from 3-furanylboronic acid
[c]Starting from diethyl 3-pyridylborane
[d]The 5-amino group is formylated during the reaction
[e]Starting from phenylboronic acid
[f]Starting from 2-nitrophenylboronic acid
[g]Starting from 2-(tributylstannyl)furane
[h]Starting from methoxylamine hydrochloride

TABLE 2

Compounds 1b–63b.

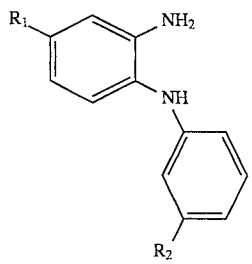

| No | R₁ | R₂ | Mp/°C. | Starting material | Example |
|---|---|---|---|---|---|
| 1b* | CF₃ | I | 182–185 | 1c | 3 |
| 2b | Me | CN | 173–174 | 2c | 3a |
| 4b | i-PrO₂C | 1-imidazolyl | ** | 4c | 4a |
| 5b | Me | 1-imidazolyl | 143–148 | 5c | 3a |
| 6b | t-Bu | 1-imidazolyl | 184–187 | 6c | 3a |
| 7b | t-Bu | 1-(4-phenylimidazolyl) | ** | 7c | 4a |
| 8b | t-Bu | 1-(4-methylimidazolyl) | ** | 8c | 4a |
| 9b | Ph | 1-imidazolyl | 210–215 | 9c | 3a |
| 10b | n-Bu | 1-imidazolyl |  | 10c | 4 |
| 11b | n-Bu | 1-(4-phenylimidazlolyl) |  | 11c | 4 |
| 12b | n-Bu | 1-(2-methylimidazolyl) |  | 12c | 4 |
| 13b* | (CH₂)₅CH | 1-imidazolyl | 175–181 | 13c | 4 |
| 14b* | i-Pr | 1-imidazolyl | 185–190 | 14c | 4 |
| 15b* | i-Pr | 1-(4-phenylimidazolyl) | 265–268 | 15c | 4 |
| 16b | i-Pr | 1-(2-methylimidazolyl) |  | 16c | 4 |
| 31b | NO₂ | Br | 177–179 | 31d | 3a |
| 32b | t-Bu | 4-morpholinyl | ** | 32c | 3a |
| 34b | i-Pr | 1-benzimidazolyl | ** | 34c | 4a |
| 35b | t-Bu | (2-amino-4-t-butyl-phenyl)amino | 222–224 | 35c | 4a |
| 37b* | t-Bu | CN | 207–208 | 37c | 4' |
| 39b | CF₃ | (2-aminophenyl)amino | ** | 39c | 4a |
| 40b* | CF₃ | acetamino | 219–221 | 40c | 4 |
| 41b* | NH₂ | 1-imidazolyl | 258–262 | 41c | 4 |
| 42b* | CF₃ | (2-amino-4-t-butylphenyl)-amino | 170–173 | 42c | 4 |
| 43b* | t-Bu | Br | 213–215 | 43c | 3 |
| 44b | t-Bu | COOH | 158–160 | 44c | 4a |
| 47b | i-PrO₂C | Br | 98–101 | 47d | 3a |
| 61b* | i-Pr | Br | 197–203 | 14d | 3 |
| 63b | cyclopropylmethoxy | Br | 122–125 | 63c | 3a |

*isolated as the hydrochloride.
**isolated as an oil.

TABLE 3

Compounds 1c–63c.

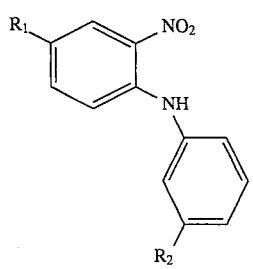

| No. | R₁ | R₂ | Mp/°C. | Starting material | Example |
|---|---|---|---|---|---|
| 1c | CF₃ | I | 98–101 |  | 5a |
| 2c | Me | CN | 162–163 |  | 2ᵇ |
| 4c | i-PrO₂C | 1-imidazolyl | ** | 4d | 2 |

TABLE 3-continued

Compounds 1c–63c.

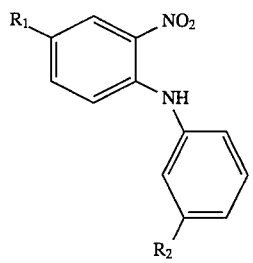

| No. | $R_1$ | $R_2$ | Mp/°C. | Starting material | Example |
|---|---|---|---|---|---|
| 5c | Me | 1-imidazolyl | 124–126 | 5d | 2 |
| 6c | t-Bu | 1-imidazolyl | ** | 6d | 2 |
| 7c | t-Bu | 1-(4-phenylimidazolyl) | ** | 6d | 2 |
| 8c | t-Bu | 1-(4-methylimidazolyl) | ** | 6d | 2 |
| 9c | Ph | 1-imidazolyl | 114–120 | 9d | 2 |
| 10c | n-Bu | 1-imidazolyl | | 10d | 2 |
| 11c | n-Bu | 1-(4-phenylimidazolyl) | | 10d | 2 |
| 12c | n-Bu | 1-(2-methylimidazolyl) | | 10d | 2 |
| 13c | $(CH_2)_5CH$ | 1-imidazolyl | ** | 13d | 2 |
| 14c | i-Pr | 1-imidazolyl | 65–66 | 14d | 2 |
| 15c | i-Pr | 1-(4-phenylimidazolyl) | 123–124 | 14d | 2 |
| 16c | i-Pr | 1-(2-methylimidazolyl) | | 14d | 2 |
| 32c | t-Bu | 4-morpholinyl | ** | | 14 |
| 34c | i-Pr | 1-benzimidazolyl | ** | 14d | 2 |
| 35c | t-Bu | (2-nitro-4-t-butylphenyl)-amino | 120–122 | | 6[c] |
| 37c | t-Bu | CN | 83–84 | | 6[b] |
| 39c | $CF_3$ | (2-nitrophenyl)amino | 95–98 | 45c | 15 |
| 40c | $CF_3$ | acetamino | 188–190 | 45c | 16 |
| 41c | $NO_2$ | 1-imidazolyl | 167–169 | 31d | 2 |
| 42c | $CF_3$ | (2-nitro-4-triflouromethyl-phenyl)amino | 133–135 | | 15 |
| 43c | t-Bu | Br | 74–76 | 6d | 6 |
| 44c | t-Bu | COOH | 194–195 | | 17 |
| 45c | $CF_3$ | $NH_2$ | 110–112 | | 15 |
| 63c | cyclopropylmethoxy | Br | 76–82 | | 6[d]/38[e] |

**isolated as an oil.
[a]commercial available starting materials are not listed.
[b]starting from 4-methyl-2-nitroaniline and 3-bromobenzonitrile.
[c]2 equivalents of 4-t-butyl-2-nitroaniline was used.
[d]using 1,3-dibromobenzene.
[e]using bromomethylcyclopropane.

TABLE 4

Compounds 4d–47d.

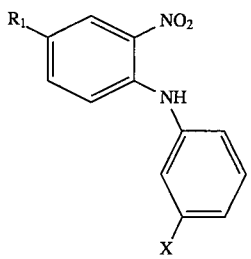

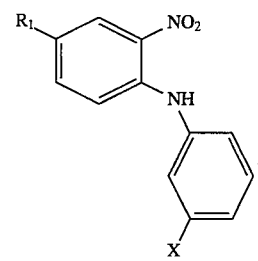

| No. | R | X | Mp/°C. | Example |
|---|---|---|---|---|
| 4d | $i\text{-}PrO_2C$ | I | 176–179 | 5a[a] |
| 5d | Me | Br | 103–104 | 6 |
| 6d | t-Bu | Br | 86–87 | 6/7 |
| 9d | Ph | Br | 109–110 | 6/8 |
| 10d | n-Bu | Br | ** | 6/7 |
| 13d | $(CH_2)_5CH$ | Br | ** | 6/7 |

TABLE 4-continued

Compounds 4d–47d.

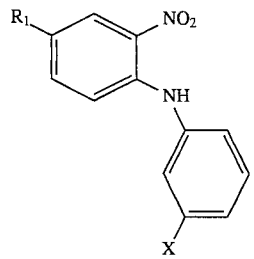

| No. | R | X | Mp/°C. | Example |
|---|---|---|---|---|
| 14d | i-Pr | Br | 51–52 | 6/7[b] |
| 31d | NO₂ | Br | 170–172 | 5a[c] |
| 47d | i-PrO₂C | Br | 162–165 | 5a[d] |

**isolated as an oil.
[a]starting from isopropyl 4-chloro-3-nitrobenzoate and 3-iodoaniline.
[b]a catalytic amount of conc. sulfuric acid was added to the acetanilide/acetic anhydride suspension prior to nitration.
[c]starting from 2,4-dinitrofluorobenzene and 3-bromaniline.
[d]starting from 2,4-dinitrofluorobenzene and 3-bromoaniline.

TABLE 5

Compounds 1f–8f.

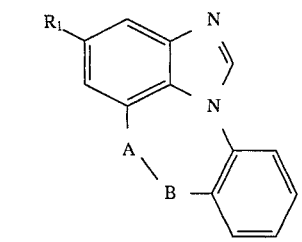

| No. | A | B | R | Mp/°C. | Starting material | Example |
|---|---|---|---|---|---|---|
| 1f | NH | C=O | CF₃ | 330–332 | | 22 |
| 2f | NMe | C=O | CF₃ | 197–198 | 1f | 23 |
| 3f | NEt | C=O | CF₃ | 173–174 | 1f | 23[a] |
| 4f | NMe | CHOH | CF₃ | 169–170 | 2f | 24 |
| 5f | N | CH | CF₃ | 242–243 | | 25 |
| 6f | not present | C=O | Me | 255–257 | | 26 |
| 7f | not present | C=O | t-Bu | 240–242 | | 26[b] |
| 8f | not present | CHOH | t-Bu | 188–190 | 7f | 24 |

[a]Using iodoethane instead of iodomethane.
[b]Starting from 4-t-butyl-2-nitroaniline. Example 7.

TABLE 6

Compounds 1g–15g.

| No. | R₁ | R₂ | R₃ | R₄ | X | Mp/°C. | Starting material | Ex. |
|---|---|---|---|---|---|---|---|---|
| 1g | H | CF₃ | 3-pyridyl | H | CH | 118–120 | 4g | 11[a] |
| 2g | H | CF₃ | 3-aminophenyl | H | CH | 202–205 | 4g | 11 |
| 3g | COCH₃ | H | H | NO₂ | CH | 175–177 | | 18 |
| 4g | H | CF₃ | I | H | CH | 118–120 | | 9 |
| 5g | NO₂ | H | H | 3-pivaloylamino | CH | 105–110 | | 19 |
| 6g | H | t-Bu | H | Br | N | 98–100 | | 20 |
| 7g | NO₂ | H | H | Br | CH | 180–182 | | 21 |
| 8g | H | CF₃ | NH₂ | Ph | CH | 70–71 | 9g | 4 |
| 9g | H | CF₃ | NO₂ | Ph | CH | 150–152 | | 9[b] |
| 10g | H | CF₃ | 3-aminophenyl | CN | CH | 211–215 | 11g | 11 |
| 11g | H | CF₃ | I | CN | CH | 174–175 | | 9[c] |
| 12g | H | CF₃ | Ph | H | CH | 174–176 | 13g | 11[d] |
| 13g | H | CF₃ | I | H | CH | 118–120 | 14g | 9[e] |
| 14g* | H | CF₃ | NH₂ | H | CH | ** | | 9[f] |
| 15g | H | CF₃ | PhCONH | H | CH | 152–155 | 14g | 37 |

*Isolated as the hydrochloride.
**Used without purification.
[a]Using diethyl 3-pyridylborane
[b]Analogueously to 4i from 4-chloro-3,5-dinitrobenzoetrifluoride and 3-aminobiphenyl.
[c]Analogueously to 4g from 4-chloro-3,5-dinitrobenzoetrifluoride and 3-aminobenzonitril.
[d]Using phenylboronic acid.
[e]Analogueously to 4g.
[f]Analogueously to 4h starting from 4-chloro-3,5-dinitrobenzoetrifluoride.

TABLE 7

Compounds 1k–11k.

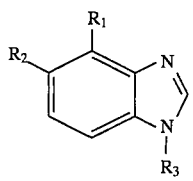

| No. | R₁ | R₂ | R₃ | Mp/°C. | Starting material | Example |
|---|---|---|---|---|---|---|
| 1k | =N—S—N= | | 3-iodophenyl | 193–195 | 11 | 1/3 |
| 2k | —CH=CH—CH=CH— | | 3-nitrophenyl | 136–138 | 3k | 31 |
| 3k | —CH=CH—CH=CH— | | H | 273–285 | 1,2-diamino-naphtalene | 1/32 |
| 4k | —CH=CH—CH=N— | | 3-nitrophenyl | 219–221 | 5k | 31 |
| 5k | —CH=CH—CH=N— | | H | 270–272 | 5,6-diamino-** quinoline | 1 |
| 6k* | —CH₂—N(CH₃)—(CH₂)₂— | | 3-nitrophenyl | 266–269 | 7k | 31 |
| 7k* | —CH₂—N(CH₃)—(CH₂)₂— | | H | 297–299 | 5,6-diamino-3-methyl-1,2,3,4-tetrahydroisoquinoline | 32 |
| 8k* | H | t-Bu | 8-isoquinolyl | 253–260 | 81 | 1/3 |
| 9k | H | CF₃ | 5-quinolyl | 181–183 | 91 | 1/4 |
| 10k | H | CF₃ | 6-quinolyl | 190–194 | 101 | 1/4 |
| 11k | H | CF₃ | 1-naphtyl | 170–173 | 111 | 1/3 |

*Isolated as the hydrochloride.
**Preparation as described in U.S. Pat. appln. Ser. No. 08/124,770 of Sept. 24, 1993

TABLE 8

Compounds 1l-11l.

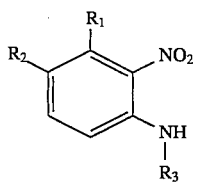

| No. | R₁ | R₂ | R₃ | Mp/°C. | Starting material | Example |
|---|---|---|---|---|---|---|
| 11 | =N—S—N= | | 3-iodophenyl | 224–225 | 4-chloro-3-nitrobenzothiadiazole | 5a |
| 81 | H | CF₃ | 8-isoquinolyl | * | 8-bromoisoquinoline | 6 |
| 91 | H | CF₃ | 5-quinolyl | 138–140 | 5-aminoquinoline | 5a |
| 101 | H | CF₃ | 6-quinolyl | 158–160 | 6-aminoquinoline | 5a |
| 111 | H | CF₃ | 1-naphtyl | 148–150 | 1-aminonaphtalene | 5a |

*Isolated as an oil.

We claim:

1. A compound having the formula:

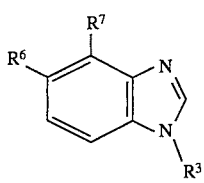

or a pharmaceutically-acceptable salt thereof wherein $R^3$ is

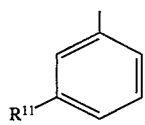

wherein one of $R^6$ and $R^7$ is $C_1$–$C_9$ acylamino; CH=NOH; CH=NO-alkyl; CH=N—NH—(C=O)—NH₂;

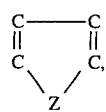

wherein Z is O, S, N, C=C, or C=N; or imidazolyl; and the other of $R^6$ and $R^7$ is hydrogen;

$R^{11}$ is selected from pyridyl, imidazolyl, and said groups having an alkyl ring substituent; and wherein alkyl is $C_1$–$C_8$ alkyl.

2. A compound of claim 1 wherein $R^3$ is

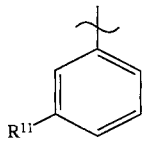

wherein $R^{11}$ is pyridyl.

3. A compound of claim 1, which is

1-[3-(3-pyridyl)-phenyl]-5-methylaldoximo-benzimidazole,

1-[3-(3-pyridyl)-phenyl]-5-(2-furanyl)-benzimidazole,

1-[3-(1-imidazolyl)-phenyl]-5-phenyl-benzimidazole,

1-[3-(1-(2-methylimidazolyl))-phenyl]-5-phenyl-benzimidazole,

1-[3-(3-pyridyl)-phenyl]-5-(1-imidazolyl)-benzimidazole,

1-[3-(1-imidazolyl)-phenyl]-5-amido-benzimidazole,

1-[3-(3-pyridyl)-phenyl]-5-aldoximo-benzimidazole, or

1-[3-(3-pyridyl)-phenyl]-5-(3-furanyl)-benzimidazole, or a pharmaceutically-acceptable salt thereof.

4. A pharmaceutical composition comprising an effective amount of a compound of claim 1, or a pharmaceutically-acceptable addition salt thereof, together with at least one pharmaceutically-acceptable carrier or diluent.

5. A pharmaceutical composition comprising an effective amount of a compound of claim 3, or a pharmaceutically-acceptable addition salt thereof, together with at least one pharmaceutically-acceptable carrier or diluent.

6. A pharmaceutical composition comprising an effective amount of a compound of claim 2, or a pharmaceutically-acceptable addition salt thereof, together with at least one pharmaceutically-acceptable carrier or diluent.

* * * * *

UNITED STATES PATENT AND TRADEMARK OFFICE
CERTIFICATE OF CORRECTION

PATENT NO. : 5,554,632      Page 1 of 4
DATED : September 10, 1996
INVENTOR(S) : L. Teuber, O. Axelsson, F. Watjen It is certified that error appears in the above-indentified patent and that said Letters Patent is hereby corrected as shown below:

Title Page, [75] Inventors:, line 1: "Varlose" should read -- Vaerlose --.

Column 2, line 66: "-5-1-" should read -- -5-i- --.

Column 4, line 60: "1-" at beginning of line should read -- 4- --.

Column 5, line 13: "acyl NH" should read -- acyl-NH --.

Column 5, line 24: "-imidazolyl" (2nd occurrence) should read -- 4-imidazolyl --.

Column 6, line 28: "GABAs" should read -- $GABA_B$ --.

Column 6, line 61: "3H-" should read -- $^3H$- --.

Column 8, line 58: "Alter, natively," should read -- Alternatively, --.

Column 10, line 40: "1-(3-idophenyl)" should read -- 1-(3-Iodophenyl) --.

UNITED STATES PATENT AND TRADEMARK OFFICE
CERTIFICATE OF CORRECTION

PATENT NO. : 5,554,632
DATED : September 10, 1996
INVENTOR(S) : L. Teuber, O. Axelsson, F. Watjen It is certified that error appears in the above-indentified patent and that said Letters Patent is hereby corrected as shown below:

Column 11, line 14: "4-1-propyldiphenylamine" should read -- 4-i-propyldiphenylamine --.

Column 11, line 29: "3'-lodo-" should read --3'-Iodo- --; and "(1c)," should read -- (1c). --.

Column 12, line 12: "4-ACetaminobipheny/-" should read -- 4-Acetaminobiphenyl. --.

Column 12, line 39: Delete the space between "trifluoromethyldiphenylamine" and "(4k)."

Column 13, line 45: "benzimidazo." should read -- benzimidazole --.

Column 13, line 46: Delete "le" from the beginning of the line.

Column 13, line 57: "appropiate" should read -- appropriate --.

Column 14, line 10: "4-t-Butyl-3'-(4-" should start a new line.

UNITED STATES PATENT AND TRADEMARK OFFICE
CERTIFICATE OF CORRECTION

PATENT NO. : 5,554,632
DATED : September 10, 1996
INVENTOR(S) : L. Teuber, O. Axelsson, F. Watjen It is certified that error appears in the above-indentified patent and that said Letters Patent is hereby corrected as shown below:

Column 14, line 12: "2nitrobenezene*" should read -- 2-nitrobenezene* --.

Column 14, line 26: "1,3phenylenediamine" should read -- 1,3-phenylenediamine --.

Column 15, line 29: "-4,nitrobenzimidazole" should read -- -4-nitrobenzimidazole --.

Column 17, line 30: "(If)" should read -- (1f) --.

Column 18, liine 1: "5h," at beginning of line, should read -- 5h. --.

Column 18, line 25: "methanolic" should read -- ethanolic --.

Column 20, line 42(approx.): "LiAlH4" should read -- $LiAlH_4$ --.

UNITED STATES PATENT AND TRADEMARK OFFICE
CERTIFICATE OF CORRECTION

PATENT NO. : 5,554,632
DATED : September 10, 1996
INVENTOR(S) : L. Teuber, O. Axelsson, F. Watjen It is certified that error appears in the above-indentified patent and that said Letters Patent is hereby corrected as shown below:

Column 20, line 57: "Mp 00° - 202°C." should read
-- Mp 200° - 202°C. --.

Column 20, line 61: Delete the "," (comma) at the end of the line and insert a -- . -- (period).

Column 29, 2nd to last liine: "bromaniline" should read -- bromoaniline --.

Signed and Sealed this

Twenty-fifth Day of February, 1997

Attest:

BRUCE LEHMAN

Attesting Officer    Commissioner of Patents and Trademarks